United States Patent [19]

Chen et al.

[11] Patent Number: 5,665,393
[45] Date of Patent: Sep. 9, 1997

[54] HERBAL COMPOSITION FOR TREATING PROSTATE CARCINOMA

[75] Inventors: Sophie Chen, Millwood, N.Y.; Xuhui Wang, Shanghai, China

[73] Assignee: International Medical Research, Inc., Brea, Calif.

[21] Appl. No.: 697,920

[22] Filed: Sep. 3, 1996

[51] Int. Cl.[6] .................................................. A61K 9/14
[52] U.S. Cl. .................. 424/489; 424/465; 424/461; 424/470; 424/464; 424/195.1; 424/436
[58] Field of Search ...................... 424/489, 470, 424/464, 461, 433, 195.11, 195.1, 436

[56] References Cited

U.S. PATENT DOCUMENTS 5,417,979  5/1995  Fan et al. ............................ 424/451

*Primary Examiner*—Thurman K. Page
*Assistant Examiner*—William E. Benston, Jr.
*Attorney, Agent, or Firm*—Charles J. Herron

[57] ABSTRACT

A composition comprising material from the following herbs: Panax pseudo-ginseng Wall, Isatis Indigotica Fort, Ganoderma lucidum Karst, Dendranthema morifolium Tzvel, Glycyrrhiza glabra L., Scutellaria baicalensis Georgi, Rabdosia rubescens, Serenoa repens. Preferably, the material from each of such herbs is an alcohol extract of dried, cut plants and of the Panax the pseudo-ginseng Wall and each of the other materials are present in a dried, weight-to-weight range of about 1:1–6. The composition is administered orally or by suppository.

9 Claims, 4 Drawing Sheets

HERBAL COMPOSITION FOR TREATING PROSTATE CARCINOMA

BACKGROUND OF THE INVENTION

Prostate carcinoma is the second leading cause of death among men. The American Cancer Society estimates that 317,000 men will be diagnosed with prostate cancer in 1996. While many of the small, localized prostate cancer appear not to be life-threatening, those that spread to other sites in the body are almost invariably fatal. The conventional treatment includes radical prostactomy, nerve-sparing prostatectomy, external-beam radiation, seed radiation, cryotherapy and hormone therapy. Each of these therapies has serious side effects and other limitations (Review: Schroder F. H., Urology, 1995 September; 46 (3 Supplement A): 62–70). The long term results show a rate of cancer recurrence after the treatment. Therefore, there is no permanent cure.

Serum PSA (Prostate Specific Antigen) is a diagnostic parameter that has been used to monitor the stages of cancer development and the progress of the therapy. Serum PSA measures the substance emitted both by the normal prostate gland and by cancerous tissue in the prostate gland. With normal prostate gland, PSA reads between 0 to 4. Elevated PSA (higher than 5) indicates a sign of prostate carcinoma, benign prostate hyperplasia or prostatitis. The higher the PSA reading, the larger the volume of the cancer (Das et al., Eds. Cancer of the Prostate, New York, N.Y., Marcel Dekker Inc., 1993).

Serenoa repens or pygeum have been used to treat benign prostate hyperplasia (Vahlensieck et al., Fortschr-Medicine, 1993, Jun. 30, 111 (18):323–326). However, it appears there has been no application of herbs for the treatment of prostatic carcinoma.

Fan and Wong, U.S. Pat. No. 5,417,979 discloses a combination of the herbs Ganoderma lucidum Karst, Rabdosia rubescens and Glycyrrhiza glabra L. with other herbs for treatment of cancers other than prostate cancer.

SUMMARY OF THE INVENTION

The present invention provides a composition of herbs and their extracts which is useful to treat prostate carcinoma and which can also be used as a dietary supplement. The combination of herbs and their extracts profoundly improve prostate cancer patients' condition, such as a decrease in their PSA, a stimulation in their immune system and an improvement in their appetite and well-being.

The composition comprises Isatis Indigotica Fort, Panax pseudo-ginseng Wall, Ganoderma lucidum Karst, Dendranthema morifoliun Tzvel, Glycyrrhiza glabra L., Scutellaria baicalensis Georgi, Rabdosia rubescens, Serenoa repens or extracts thereof. Preferably, the material from each of such herbs is an alcohol extract of dried, cut plant parts. It is particularly preferred that the Panax pseudo-ginseng Wall and each of the other materials are present in a dried, weight-to-weight range of ratios of about 1:1–6.

The composition of the invention is preferably provided in an ingestible form, such as, for example, a powder, capsule or tablet. Alternatively, the composition can be provided in the form of a suppository.

The invention further provides a method of treating prostate cancer in an individual in need thereof which comprises administering a therapeutically effective amount of the composition described herein.

The invention further provides such a method which further comprises administering a therapeutically effective amount of a compound selected from the group consisting of luteinizing hormone releasing hormone, estrogen, antiandrogen, gonadotrophin-releasing hormone and synthetic analogs thereof which have hormone activity.

The invention further provides such a method which further comprises administering a therapeutically effective amount of a compound selected from the group consisting of antibiotics, antimetabolites and cytotoxic agents.

DETAILED DESCRIPTION OF PREFERRED EMBODIMENTS

Figure 1:
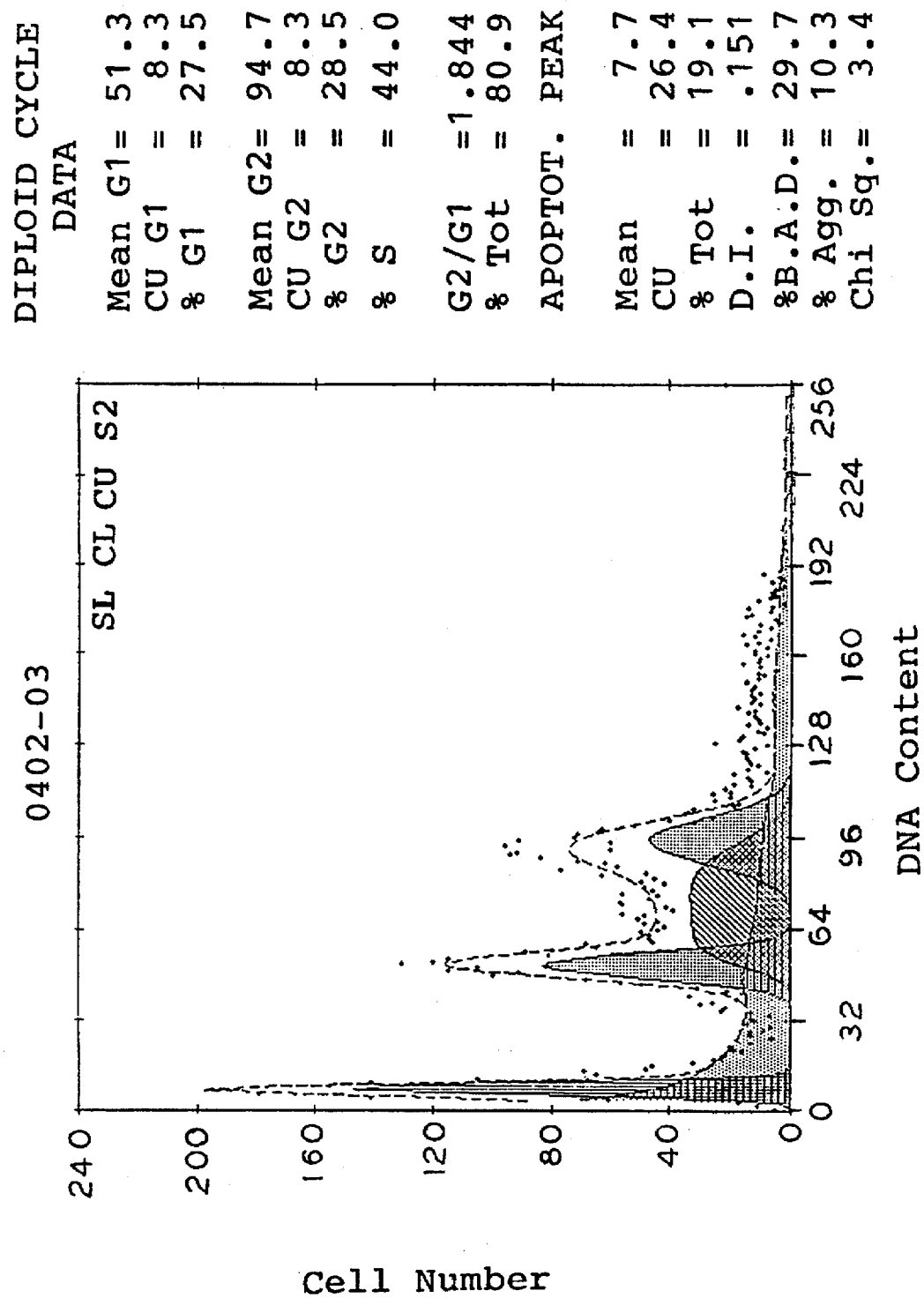
FIG. 1 graphically illustrates the DNA histogram of PC3 cell (Prostate cancer cell line) in the presence of herbal extracts for 48 hours as discussed in example 2. The histogram reflects the DNA content of the cancer cell at different stage of the cell cycle. Cells in G2 and M phases of the cell cycle have double the DNA content when incubated with the composition of the invention for 48 hours. Simultaneously, cells in S phase and G1 phase decrease.

In this invention, groups of herbs were specifically chosen and combined according to their biological activities. Although each herbal component selected in this group has been well characterized and used before, their combination for the treatment of prostate carcinoma is a new concept. As a holistic approach to combatting prostate cancer, we select herbs which possess the following biological activities: (1) Anti tumor activity; (2) Immune stimulating activity; (3) Anti viral activity; (4) Anti inflammatory activity; and (5) Anti benign prostate hyperplasia. Below are the categories of herbs used in this invention based on the published studies. Most of the herbs have multifunctional activities.

1. Anti tumor activity:
   A) Ganoderma lucidum Karst: Maruyama et al., J. Pharmacobiodyn, 1989, February 12 (2):118–23.
   B) Robdosia ruberscens: Wang et al., Chung Hun-Chung-Liu-Tsa-Chih, 1986 July; 8(4):297–9.
   C) Scutellaria baiculennsis Georgi: Konoshitna et at., Chem Phar. Bull. Tokoyo 1992, February 40 (2):531–3.
2. Immune stimulating activity:
   A) Ganoderma lucidum Karst: Ed. New Medical College od Jian-Su Province, Encyclopedia of Chinese Medicinal Herbs, 1975, pp. 2395–99, by Shanghai People's Publisher.
   B) Isatis Indigotica Fort: Xu et at., Chung-Hsi-I-Chieh-Ho-Tsa-Chin, 1991, June 11 (6):357–9, 3225–6.
3. Anti vital activity:
   A) Scuteliana baicalenosis Georgi: Nagai et al., Biol. Pharm. Bull. 1995, February 18 (2):285–9. Li ot oi, Cell Mol. Biol. Res. 1993:39:(22):119–24.
   B) Dendranthema (Chrysanthemum) Morifolium Tzvel: He et al., J. Natural Product, 1994 January 57 (1):42–51.

4. Anti inflammatory activity:
   A) Scutellaria baicalensis Georgi: Butenko et al., Agents Actions, 1993, 39 Spec. No.: 49–51.
   B) Blycyrrhiza glabra L.: Kobayashis et al., Biol. Pharm. Bull. 1995 October 18 (10):1382–5.
5. Anti Benign prostate hyperplasia activity:
   Serenca repens: Dralkorn et al., Urologe A., 1995. 34(2):119–29.

The alcohol extracts of the above herbs were obtained in the lyophilized powder form and were mixed and encapsulated in capsules. They were taken orally as dietary supplement.

The weight of panax pseudo-ginseng Wall was defined as 1, the wight ratio of Isatis indigotica Fort was from about 1 to about 4, of Ganoderma lucidum Karst was from about 1 to about 6, of Dendranthema morifolium Tzvel was from about 1 to about 4, of Glycyntiza glabra L was from about 1 to about 4, of Scutellaria balcalensis Georgi was from about 1 to about 4, of Robdosia rubersens was from about 1 to about 6, of Serenca repens was from about 1 to about 6.

EXAMPLE 1

Preparation of Extract Composition

A preferred formulation of the composition of the invention is prepared to contain the following: Isatis indigotica Fort, Panax pseudo-ginseng Wall, Ganoderma lucidum Karst, Scutellaria baicalensis Georgi, Dendranthema morifolium Tzvel, Glycyrrhiza glabra L., Robdoisa ruberscens, Serenoa repens:

The alcohol extracts of the first seven herbs above were purchased from Shanghai Medical College of Traditional Chinese Medicine (Shanghai, China). They were obtained as powder form. The powder of Sernoa repens was purchased from Frontier Cooperative Herb (Norway, Ind. 52318).

The above herbal powders were combined and mixed in a powder mixer (Won-Nen Mixer, Model 8L-K-III, Shanghai). The weight of panax pseudo-ginseng Wall was defined as 1, the relative weights of the rest of the ingredients were from 1 to 6.

EXAMPLE 2

Effect of Herbal Extract on Cell-Cycle Progression of Prostate Carcinoma Cell Line PC 3

Preparation of Herbal Solution

From the composition prepared as described in Example 1,300 mg was dissolved in 1.0 mL of absolute ethanol and incubated at 37° C. for one hour. Ethanol extract of the herbal mixture was filtered through 0.2 micron Millipore filter and used as stock solution. All dilutions were made with the cell culture medium MEM and 10% serum purchased from Gibco BRL, Grand Island, N.Y.).

Cell Line

PC 3 prostate cancer cells (ATCC #CRL 1435) were used in this study. All cells were washed twice with buffered saline and were resuspended in RPMI 1640 medium (Gibco) supplemented with 10% fetal bovine serum and 100 units/ml penicillin, 100 ug/ml streptomycin and 2 mM L-glutathoine at a density of $10^9$ cells/mL and cultured in the presence of 10 ug.mL of phytohemagglutinin (PHA, Sigma, St. Louis, Mo.).

Results:

Cells were incubated with the herbal extract in concentrations of 0.01 to 4 µL per mL of culture medium. The incubation times were 24 and 48 hours. After incubation, the cells were washed with Hank's balanced salt solution (HBSS) and the cells were fixed in ice-cold 70% ethanol.

Aliquots of fixed cells were rehydrated into HBSS and then stained with 1.0 µg/ml DAPI and 10 µg/mL sulforhodamine 101 (Eastman Kodak, Rochester, N.Y.).

The blue DNA-specific DAPI fluorescence and red protein-specific sulforhodamine fluorescence were detected by a flow cytpmeter (Ortho diagnostic, Weswood, Mass.). The data from 0.5 to $1.0 \times 10^5$ cells were collected and the DNA histograms deconvoluted.

Figure 2:
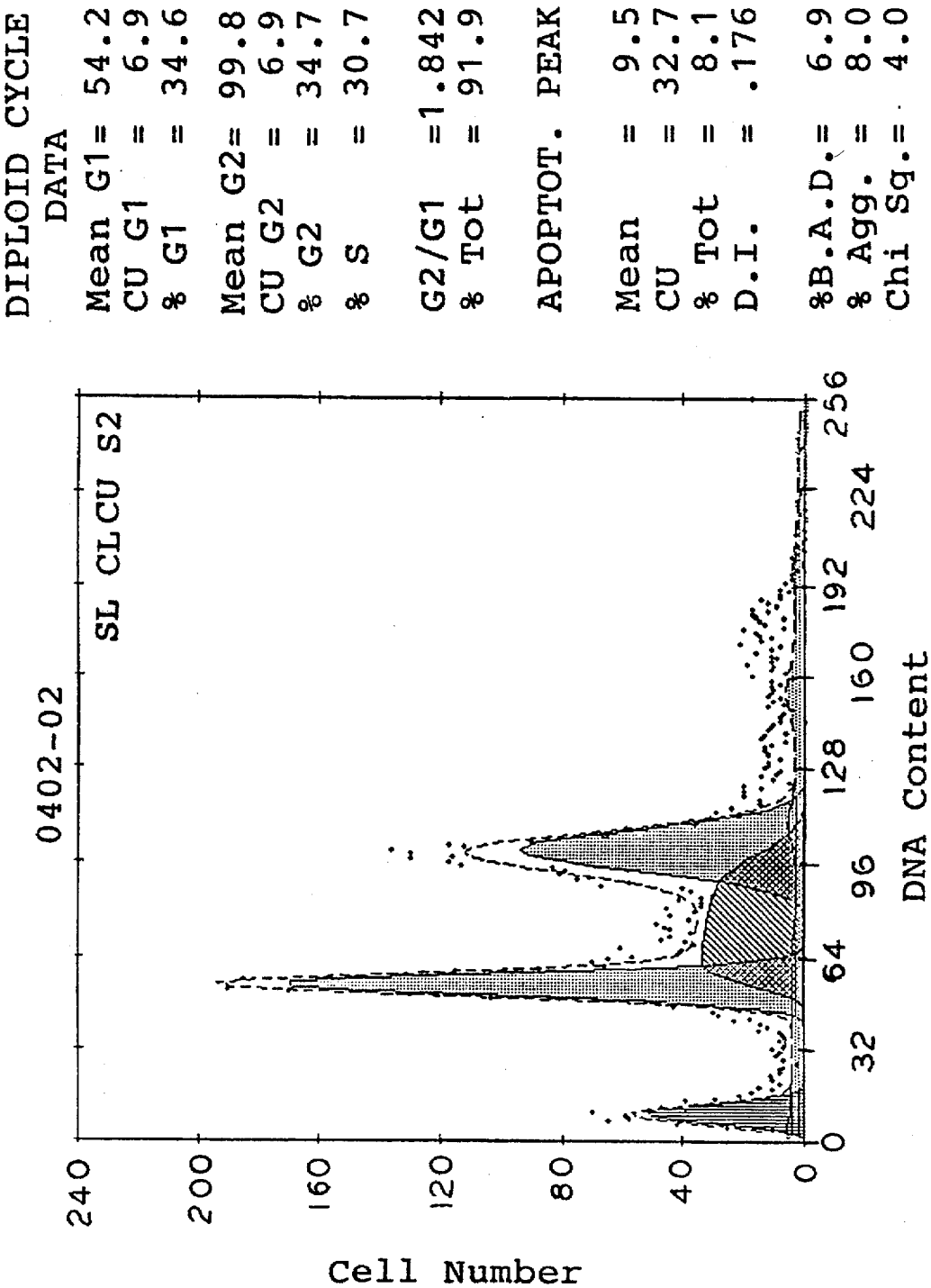
FIG. 2 shows the histogram of PC 3 cells in the absence of the herbal extract at 48 hours. No apparent change in the cytogram was observed.
Figure 3:
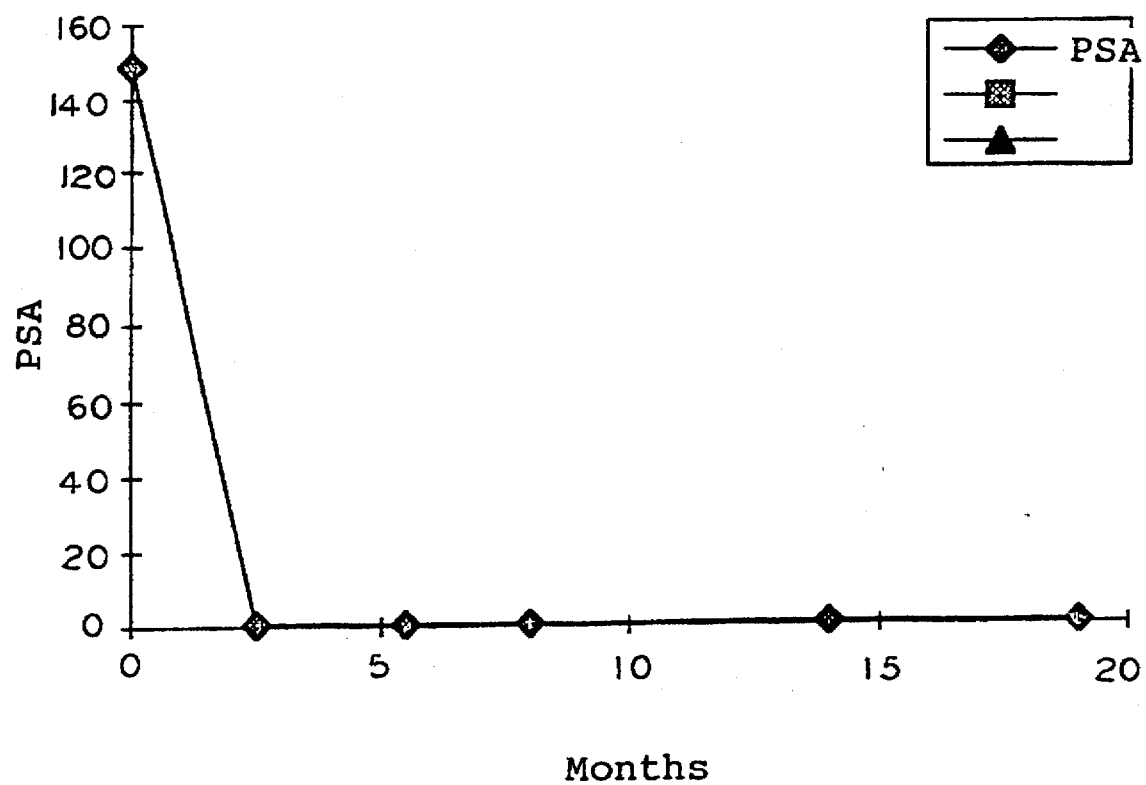
FIG. 3 shows the decrease in PSA as a function of time after oral administration of the herbal preparation of the invention as described in Example 3, in combination with hormone therapy.
Figure 4:
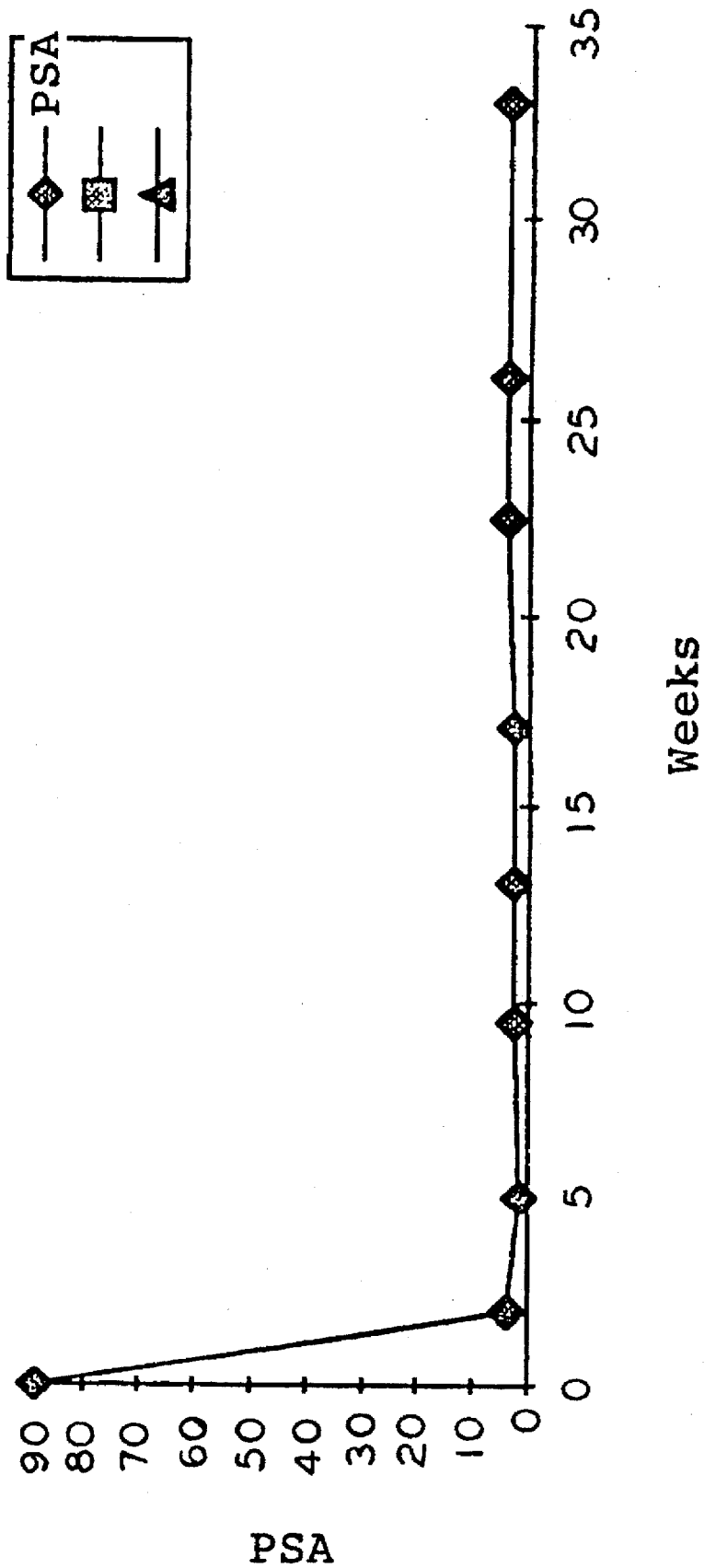
FIG. 4 shows the decrease in PSA as a function of time after oral administration of the herbal preparation of the invention alone as described in Example 4.

As illustrated in Table 1, FIG. 1 and FIG. 2, a profound decrease in the % of both S and G1 phases was seen both at 48 hr. Accumulation of cells in G2M phase from 36 to 67 was observed in the treated cells. Furthermore, percentage for cancer cell apoptosis also increased in the treated cell population. In contrast, no apparent change in the DNA cystogram was observed in the absence of herbal extract at 48 hours.

TABLE 1

| Cell Line | Herbs (µL/mL) | Cell Cycle Distribution | | |
|---|---|---|---|---|
| | | G1 | S | $G_2M$ |
| PC3 | 0 | 34 | 30 | 36 |
| PC3 | 2.0 | 20 | 13 | 67 |

These results demonstrate the potency of herbal extract in inducing cancer cell death as well as in inhibiting cancer cell proliferation.

EXAMPLE 3

Clinical Study: Case 1

The patient in this case study was a 72 year old Asian male (in Taiwan). A biopsy was performed at Taiwan Veteran's Hospital (TVH) in Taipei on Day 1. The pathology report and bone scan indicated a prostate carcinoma metastasized to bone. The PSA was measured to be 182.

Hormone therapy was begun on the patient on day 15, and included a subcutaneous injection of 3.6 mG Zoladex (goserelin acetate implant) once per month, and an oral administration of 250 mG of Eulexin (flutamide) 3 times per day. At that time the PSA level was 172. The treatment continued for 3 months and the follow-up blood test (on Day 105) indicated a serum PSA of 149. Hormone therapy improved patient's condition only slightly.

In addition to hormone therapy, the patient started a new alternative therapy by oral administration of the herbal formula of the present invention. The intake dosage of the herb composition was 1200 mG per day. This combination treatment continued for two and one-half months. During this period, the patient's appetite improved and his energy and well-being were enhanced. There was no apparent adverse effect reported. On Day 182, a follow-up serum PSA of 0.84 was reported.

The same medication was continued for another 3 months. A follow up blood test (two weeks later) showed a constant PSA reading of 0.84.

The same medication was continued for another three months. At the time, a follow-up bone scan showed almost complete resolution of multiple bone metastases.

The same treatment was continued for another six months. At the time, a follow-up serum PSA was measured to be 0.84. The results of the bone scan reported that the appearance and the function of the prostate, bladder and urethra were normal.

The dosage of the herbal formula was then reduced to 600–300 mG per day. The reduced dosage was able to maintain the patients' healthy status. At present, the patient lives a healthy and active life.

EXAMPLE 4

Clinical Study: Case 2

A white male, age 73, presented for a bone scan and biopsy which revealed extensive bony metastatic disease involving the spine, pelvis, ribs, left scapula, right clavicle and midshaft of the left femur. Serum PSA was measured to be 1027.8

One week later, the patient started hormone treatment; regular subcutaneous injection of Lupron (leuprolide acetate) every 28 days and 750 mG of Eulexin (flutamide) per day where begun. The medication was continued for two and one-half months. At that time, a follow-up serum PSA measured to be 0.9. The patient was responding well to the drag therapy.

That same medication was continued, but after about three (3) years the patient's PSA had increased to 6.4.

Six (6) months later, a repeat PSA test found a PSA level to 28.9. At this time, Lupron was continued but the Eulexin was discontinued.

Nine (9) months later, serum PSA was found to be 32.8. Three weeks later, hydrazine sulfate was added to the Lupron treatment regimen.

Six (6) months later, PSA was found to be 52.8. Hydrazine sulfate was discontinued and a new treatment regimen was started: 600 nG of Nizoral (ketoconazale) and 5 mg of prednisone per day.

Six (6) months later, serum PSA was 4.8 and the patient discontinued taking Nizoral and prednisone. The only medication received was Lupron. Three (3) months later, serum PSA had elevated to 89.0.

Three (3) months later, the patient started taking the herbal preparation of the present invention. Dosage: 1800 mG per day. One week later, the dosage of the herbal formula was increased to 2700 mG per day.

The following week, the patient's serum PSA was measured to be 3.8. The dosage for the herbal preparation was also decreased to 1800 mG per day. The patient received only ½ the dosage of Lupron.

A one-month follow-up of serum PSA was measured to be 1.6 (normal). The dosage for the herbal formula was reduced to 900 mG per day. In addition, Lupron was reduced to one-third dosage.

Two (2) months later, a follow-up PSA showed normal, 2.77. Lupron treatments had been discontinued.

Twelve (12) days later, a follow-up PSA level of 2.73 was observed and the dosage of the herbal formula was again reduced to 600 mG. No other medication was given. The patient continued 600 mG of herbal formula daily.

Thereafter, the patient's serum PSA has stabilized in the range from 2.73 to 3.9 since, by taking only 300–600 mG of the composition of the present invention.

What is claimed is:

1. A composition comprising material from the following herbs: Panax pseudo-ginseng Wall, Isatis Indigotica Fort, Ganoderma lucidum Karst, Dendranthema morifolium Tzvel, Glycyrrhiza glabra L., Scutellaria baicalensis Georgi, Rabdosia robescens and Serenoa repens.

2. The composition of claim 1, wherein the material from each of such herbs is an alcohol extract of dried, cut plant parts.

3. The composition of claim 2, wherein the Panax pseudo-ginseng Wall and each of the other materials are present in a dried, weight-to weight range of about 1:1–6.

4. The composition of claim 1 in an ingestible form.

5. The composition of claim 4 wherein the ingestible form is selected from a powder, capsule, tablet.

6. The composition of claim 1 in the form of a suppository.

7. A method of treating prostate cancer in an individual in need thereof which comprises of administering a therapeutically effective mount of the composition of claim 1.

8. The method of claim 7 which further comprises administering a therapeutically effective amount of a compound selected from the group consisting of:
luteinizing hormone releasing hormone, estrogen, antiandrogen, gonadotrophin-releasing hormone and synthetic analogs thereof which have hormone activity.

9. The method of claim 7 which further comprises administering a therapeutically effective mount of a compound selected from the group consisting of antibiotics, antimetabolites and cytotoxic agents.

* * * * *